United States Patent [19]

Labows et al.

[11] 4,349,626

[45] Sep. 14, 1982

[54] METHOD OF DETECTING PSEUDOMONAS AERUGINOSA INFECTIONS UTILIZING SELECTED KETONE AND/OR SULFUR METABOLITES

[75] Inventors: John N. Labows, Horsham; James G. Kostelc, Glenside; Kenneth J. McGinley, Philadelphia, all of Pa.

[73] Assignee: The Monell Chemical Senses Center, Philadelphia, Pa.

[21] Appl. No.: 201,565

[22] Filed: Oct. 28, 1980

[51] Int. Cl.$^3$ .......................... C12Q 1/10; C12R 1/385
[52] U.S. Cl. ........................................ 435/38; 435/875
[58] Field of Search .................................. 435/38, 875

[56] References Cited

PUBLICATIONS

Moss, C. W. and S. B. Dees, 1976 "Cellular Fatty Acids and Metabolic Products of Pseudomonas Species Obtained from Clinical Specimens"; Journal of Clinical Microbiology 4: 492–502.

Wade, T. J. and R. J. Mandel, 1974, "New Gas Chromatographic Charecterization Procedure: Preliminary Studies on Some Pseudomonas Species" Applied Microbiology 27: 303–311, Feb. 1974.

Charles D. Cox and J. Parker, "Use of 2-aminoacetophenone Production in Identification of *Pseudomonas aeruginosa*", Apr. 1979 9: 479–484, Journal of Clinical Microbiology.

"Development of Specific Tests for Rapid Detection of E. coli and Species of Proteus in Urine", by N. J. Hayward, et al., Journal of Clinical Microbiology, Sep. 1977 6: 195–201.

"Volatile Compounds Produced in Sterile Fish (*Sebastes malanops*) by Pseudomonas putrefaciens, Pseudomonas fluorescens, and an Archromobater Species", by Miller et al., Applied Microbiology, 26: 18–21 Jul. 1973.

"High Resolution Gas Chromatographic Profiles of Volatile Organic Compounds Produced by Microorganisms at Refrigerated Temperatures", by Lee, et al., Applied and Environmental Microbiology No. 1 37: 85–90, Jan. 1979.

"Epidemiology of *Pseudomonas aeruginosa* Infections:

Determination by Pyocin Typing", by Brunn, et al. (1976), Journal of Microbiology, 3:264–271.

"Pseudomonas Carrier Rates of Patients with Cystic Fibrosis and of Members of their Families", by Laraya-Cuasay, et al., Journal of Pediatrics, 89:23–26 (1980).

"Gas Chromatography Application in Microbiology and Medicine", by Mitruka (1979), John Wiley and Sons, New York, Chapter 13, pp. 352–374.

"Further Studies on the Differentiation of *Clostridium sordelli* from *Clostridium bifermentans* by Gas Chromatography", (1970), Canadian Journal of Microbiology 16:1071–1078 Brooks, et al.

"Analysis by Gas Chromatography of Hydroxy Acids Produced by Several Species of Neisseria", Canadian Journal of Microbiology 18:157–168 (1972) Brooks, et al.

"Analysis by Gas Chromatography of Fatty Acids found in Whole Cultural Extracts of Neisseria Species", Can. J. Microbiol. 17:531–541 (1970).

"Botulism: A Pyrolysis–Gas–Liquid Chromatographic Study", J. Chromatogr. Sci. 16: 623-629 (1978).

"Quantitative Methods for the Gas Chromatographic Characterization of Acidic Fermentation By–Products of Anaerobic Bacteria", by Bohannon, et al., J. of Chromatogr. Sci. 16: 28–35 (1978).

"Analysis of Amines and Other Bacterial Products by Head–Space gas Chromatography" by Larsson, et al., Acta Path. Microbiol. Scand. Section B 86: 207–213.

"Methylmercaptan and DMDS Production from Methionine by Proteus Species Detected by Head–Space Gas-Liquid Chromatography" by Hayward, et al., J. of Clin. Microbiol. 6: 187–194 (1977).

"Characteristic Gamma–Lactone Odor Production of the Genus *Pityrosporum*" by Labows, et al., Appl. and Environ. Micro. 38: 412–415 (1979).

"The Chemistry of Some Microbially–Induced Flavor Defects in Milk and Dairy Foods", by Morgan, Biotech. Bioeng. 18:953–965 (1976).

Kostelc, et al. "Salivary Volatiles as Indicators of Periodontitis" J. Periodont. Res. 18: 185–192 (1980).

Matsumota, et al., "Identification of Volatile Compounds in Human Urine", J. Chromatogr. 85: 31–34 (1973).

Zlatkis, et al., "Concentration and Analysis of Volatile

Urinary Metabolites" J. Chromatogr. Sci. 11:299-302 (1973).

Liebich, et al., "Volatile Substances in Blood Serum: Profile Analysis and Quantitative Determination" J. Chromatogr. 142: 505-516 (1977).

van den Dool, et al., "A Generalization of the Retention Index System Including Linear Programmed Gas-Liquid Chromatography", J. of Chromatography, vol. 11, pp. 463-471 (1963).

Withycombe, et al., "Isolation and Identification of Volatile Components from Wild Rice Grain" J. of Agricultural Food Chemistry, vol. 6, pp. 816-821 (1978).

Tonzetich, "Direct Gas Chromatographic Analysis of Sulfur Compounds in Mouth Air in Man", Archives of Oral Biology, vol. 16, pp. 587-597 (1971).

Budzikiewicz, et al., "Mass Spectrometry of Organic Compounds", p. 155, Holden-Day, Inc., San Francisco (1967).

Dwivedi, et al. "Carbonyl Production from Lipolyzed Milk Fat by the Continuous Mycelial Culture of *Penicillium roqueforti*", J. Food Science, 39: 83-137 (1974).

Burger et al., "Ketones from the Pedal Gland of the Bontebok", Z. Naturforsch C: Bioscience 316: (1-2):-21-8.

Albone et al., "Bacteria as a Source of Chemical Signals in Mammals", reprinted pp. 35-43 in D. MullerSchwarze and M. M. Mozell, editors, Chemical Signals in Vertebrates, Plenum Press, N. Y. (1977).

Ikeshoji, "Bacterial Production of the Ovipositional Attractants for Mosquitos on Fatty Acid Substrates", Appl. Ent. Zool. 10:239-242.

John N. Labows, K. J. McGinley, Guy F. Webster, & J. J. Leyden, "Headspace Analysis of Volatile Metabolites of *Pseudomonas aeruginos* and Related Species by Gas Chromatography-Mass Spectrometry".

Gorbach, S. L., J. W. Mayhew, J. G. Bartlett, H. Thadepalli, and A. B. Onderdonk. 1976, Rapid Diagnosis of Anaerobic Infections by Direct Gas-Liquid Chromatography of Clinical Specimens. J. Clin. Invest. 57:478-484.

*Primary Examiner*—Robert J. Warden
*Attorney, Agent, or Firm*—Woodcock, Washburn, Kurtz, Mackiewicz & Norris

[57] ABSTRACT

A novel method of detecting and diagnosing *Pseudomonas aeruginosa* infections by monitoring sample headspace concentrations of selected methyl ketones, particularly 2-nonanone and 2-undecanone. In an alternate embodiment, such diagnosis may be made by monitoring the headspace concentration of methyl mercaptan to diagnose the extent of a *Pseudomonas aeruginosa* infection. Expeditious methods for increasing such concentrations are also disclosed which include additions of selected nutrients to incubated sample mixtures.

30 Claims, 3 Drawing Figures

METHOD OF DETECTING *PSEUDOMONAS AERUGINOSA* INFECTIONS UTILIZING SELECTED KETONE AND/OR SULFUR METABOLITES

BACKGROUND OF THE INVENTION

The present invention relates to the field of diagnosing infections of *Pseudomonas aeruginosa* through the analysis of characteristic volatile metabolites associated with such infections.

*Pseudomonas aeruginosa* is an opportunistic pathogen which is responsible for serious skin infections in burn patients and for debilitating lung infections in patients with cystic fibrosis. This pathogen is also the cause of many wound and urinary tract infections, and accounts for about 15% of all hospital-acquired infections. Early detection of the nature and extent of such infections is important to the overall treatment of infected patients.

Several approaches have previously been suggested for determining the nature and extent of *Pseudomonas aeruginosa* infections in subject patients. It has been suggested to culture the *Pseudomonas aeruginosa* for extended periods of time (between 24-48 hours) on a suitable medium, and ultimately to subject the cultures to various chemical tests and morphologic examinations. The chemical tests are based upon the fact that each organism has unique metabolic capabilities ie., sugar fermentation and oxidation, amino acid decarboxylase and dihydrolase production, $H_2S$ generation, etc. Unfortunately, such methods are slow and laborious, and may not provide diagnostic indications which are prompt enough to facilitate optimum treatment of the infection.

It has also been suggested to detect the fluorescence of various Pseudomonas by-products on the skin of burn patients in an attempt to quantify the nature and extent of *Pseudomonas aeruginosa* infections. Quantification of the extent of such infections through this method is, of course, difficult, and at present, such methods have not been successfully adapted for use in diagnosing the nature and extent of such infections in cystic fibrosis patients.

Various investigators have suggested that *Pseudomonas aeruginosa* may be identified through its secondary metabolites. It has been suggested, for example, that various Pseudomonas species including *Pseudomonas aeruginosa* may be identified through various cellular fatty acids produced by such species. See for example, Moss, C. W. and S. B. Dees, 1976, "Cellular fatty acids and metabolic products of Pseudomonas species obtained from clinical specimens"; Journal of Clinical Microbiology 4: 492-502. It has also been suggested that methyl esters of such fatty acids may be identified using gas chromatographic characterization procedures. See Wade, T. J. and R. J. Mandel, 1974, "New gas chromatographic characterization procedure: preliminary studies on some Pseudomonas species", Applied Microbiology 27: 303-311.

It has further been indicated that 2-amioacetophenone may be a useful indicator of *Pseudomonas aeruginosa* when cultures of *Pseudomonas aeruginosa* are subjected to an ether extraction of the culture and a subsequent GC/MS analysis. The results of such analysis are then compared to a known profile of 2-aminoacetophenone to determine the nature and extent of any *Pseudomonas aeruginosa* infection. See "Use of 2-aminoacetophenone production in identification of *Pseudomonas aeruginosa*", by Charles D. Cox and J. Parker, Journal of Clinical Microbiology, Vol. 9, No. 4, pgs. 479-484 (April, 1979). Similarly, in media supplemented with methionine, *Pseudomonas aeruginosa* has been reported as producing dimethyldisulfide, but not methyl mercaptan. See "Development of specific tests for rapid detection of *E. coli* and species of Proteus in urine", by N. J. Hayward, et al, Journal of Clinical Microbiology, Vol. 6, No. 3, pgs. 195-201 (September, 1977). Other species of Pseudomonas, such as *P. putida, P. fluorescens,* and *P. putrefaciens* have variously been reported as showing the presence of 2-nonanone, dimethyldisulfide, dimethyltrisulfide, and other sulfur metabolites. See "Volatile Compounds Produced in Sterile Fish Muscle (*Sebastes malanops*) by *Pseudomonas putrefaciens, Pseudomonas fluorescens,* and an Achromobacter Species", by Miller et al, Applied Microbiology, Vol. 26, No. 1, pgs. 18-21 (July, 1973). See also "High resolution gas chromatographic profiles of volatile organic compounds produced by microorganisms at refrigerated temperatures", by Lee et al, Applied and Environmental Microbiology, Vol. 37, No. 1, pgs. 8590 (January, 1979).

Other literature of particular interest in this area includes articles entitled "Epidemiology of *Pseudomonas aeruginosa* infections: determination by pyocin typing", by Bruun et al, (1976) Journal of Clinical Microbiology, 3:264-271; and "Pseudomonas carrier rates of patients with cystic fibrosis and of members of their families", by Laraya-Cuasay et al, Journal of Pediatrics, 89:23-26 (1980).

Recently, the application of gas chromatography to the indentification of unknown microorganisms has received wide-spread attention. See "Gas chromatography application in Microbiology and medicine", by Mitruka (1979), John Wiley and Sons, New York. The techniques which have been developed are based on analysis of either the unique metabolites of a given organism or on its individual structural components. Culture extracts have, for example, revealed specific amines for Clostridia (Brooks et al), "Further studies on the differentiation of *Clostridium sordelli Clostridium bifermentans* by gas chromatography", (1970) Can. J. Microbiol. 16: 1071-8. Specific hydroxy acids and fatty acids have been identified for Neisseria. Brooks et al, "Analysis by gas chromatography of hydroxy acids produced by several species of Neisseria", Can. J. Microbiol. 18: 157-168 (1972); Brooks et al, "Analysis by gas chromatography of fatty acids found in whole cultural extracts of Neisseria species", Can. J. Microbiol. 17: 531-541. As mentioned above, bacteria cellwall preparations have been examined for unique fatty acid profiles, including such profiles for Pseudomonads. Moss, supra. (1976); and Wade, supra. (1974). Pyrolysis-gas chromatography of whole cell Clostridia bacteria has also been reported as giving identifiable differences in the observed fragmentation patterns. Reiner, et al, "Botulism: A pyrolysis-gas-liquid chromatographic study", J. Chromatogr. Sci. 16: 623-629 (1978).

Headspace analysis techniques have also been developed to sample directly the volatile metabolites produced in culture. These have involved either sampling the culture headspace directly, as in the case of aliphatic acids and amines for various anaerobes, and sulfides for proteus; or have made use of volatile concentration methods such as for Pityrosporum. For literature reporting on such techniques, please refer to Bohannon et al, "Quantitative methods for the gas chromatographic characterization of acidic fermentation by-products of anaerobic bacteria", J. of Chromatogr. Sci. 16: 28–35 (1978); Larsson, et al, "Analysis of amines and other bacterial products by head-space gas chromatography", Acta Path. Microbiol. Scand. Sect B 86: 207–213; Hayward, et al, "Methylmercaptan and DMDS production from methionine by Proteus species detected by headspace gas liquid chromaography", J. of Clin. Microbiol 6: 187–94 (1977). See also Labows, et al, "Characteristic Gamma-Lactone ordor production of the genus Pityrosporum", Appl. and Environ. Micro 38: 412–415 (1979); Lee, et al, supra. (1979); and Morgan, "The chemistry and some microbially-induced flavor defects in milk and dairy foods", Biotech. Bioeng. 18: 953–965 (1976). Headspace analysis has also been applied to samples of human body fluids including salvia, urine and blood serum. For references on this topic, please refer to Kostelc, et al, "Salivary volatiles as indicators of periodontitis", J. Periodont. Res. 18: 185–192 (1980); Matsumota, et al, "Indentification of volatile compounds in human urine", J. Chromatogr. 85: 31–34 (1973); Zlatkis, et al, "Concentration and analysis of volatile urinary metabolites", J. Chromatogr. Sci. 11: 299–302 (1973); Liebich, et al, "Volatile substances in blood serum: profile analysis and quantitative determination", J. Chromatogr. 142: 505–516 (1977).

It has further been suggested to manipulate the production of secondary metabolite production in Pseudomonas through the systematic optimization of medium composition or growth conditions, or by mutation. For example, it has been suggested to alter pyocyanine production by providing a selected supply of $Fe^{2+}$, or altered amounts of phosphates. See Leisinger, et al, supra. at 435–436.

SUMMARY OF THE INVENTION

The present invention provides novel methods for diagnosing the nature and extent of *Pseudomonas aeruginosa* infections. Such methods include the collection of samples of material associated with the sites of a suspected infection, collecting volatile compounds released from such samples to provide a sample headspace, and analyzing such headspace to determine at least the concentration of at least one methyl ketone, such as 2-nonanone or 2-undecanone, contained within such headspace. The detected concentrations of such ketones are relatively proportional to, and thus diagnostically indicative of, the nature and extent of any *Pseudomonas aeruginosa* infections.

Alternatively, volatile compounds may be analyzed for their methyl mercaptan concentration. Although in certain samples, methyl mercaptan concentrations may indicate the presence of other bacteria, concentrations of methyl mercaptan will generally reflect infectious levels of *Pseudomonas aeruginosa*. When used in combination with other indicators, methyl mercaptan levels may confirm or quantify *Pseudomonas aeruginosa* infections.

In accordance with alternate embodiments of the present invention, test samples may be incubated for preselected periods of time prior to analysis. In this manner headspace concentrations of the subject ketones and/or methyl mercaptan may be predictably increased to readily quantifiable levels. In order to further enhance such concentrations, nutrient additions may be made to such samples prior to incubation. Such nutrients include decanoic acid to increase 2-nananone concentrations, dodecanoic acid to increase undercanone concentrations and methionine to increase methyl mercaptan (and other sulfur compound) concentrations.

The above described methods provide comparatively rapid, organism-specific diagnostic tests. They are particularly useful with samples of breath, saliva, sputum, urine or skin, and should facilitate optimal treatment of *Pseudomonas aeruginosa* infections.

Accordingly, a primary object of the present invention is the provision of a simple, organism-specific test for determining the extent of *Pseudomonas aeruginosa* infections.

A further object of the present invention is the provision of methods which enhance the headspace concentrations of selected volatile compounds associated with infection-associated *Pseudomonas aeruginosa* samples.

These and other objects of the present invention will become apparent from the following more detailed description.

DESCRIPTION OF THE PREFERRED EMBODIMENTS

Figure 1:
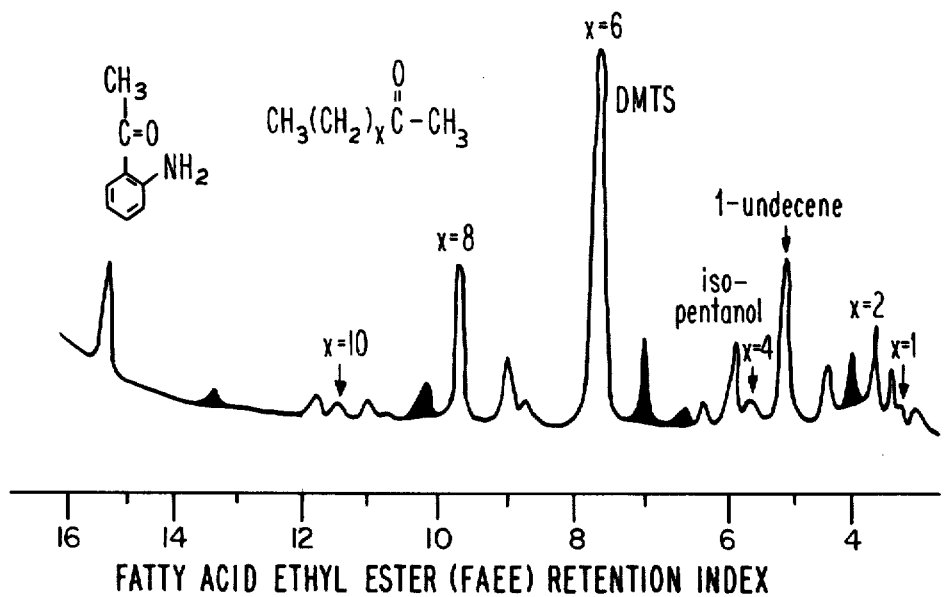
FIG. 1 is a volatile profile of *Pseudomonas aeruginosa* shown against the fatty acid ethyl ester (FAEE) retention index, and having indications imposed thereon which indentify various peaks, particularly methyl ketone peaks, of that profile.

While in the following description, specific examples and techniques have been selected for purposes of illustration, one of ordinary skill in the art will recognize that various departures from the materials, methods, techniques and examples set forth hereinafter made be made without departing from the scope of the invention, which is defined more particularly in the appended claims.

*Pseudomonas aeruginosa* is only one of a number of closely related species of Pseudomonads. An accurate diagnostic test for *P. aeruginosa* should be capable of distinguishing *P. aeruginosa* from such other strains as *P. putrefaciens, P. maltophilia, P. fluorescens, P. cepacia*, and *P. putida*. Accordingly, various strains of *Pseudomonas aeruginosa* were obtained from the American Type Culture Collection (ATCC). These strains included ATCC #19660, 7700, 17423, 27313, 27312, 27316, 17429, 17423, 7701. Further strains from the Center for Disease Control (CDC) were obtained which included strains 9104 and 9171. ATCC strains *P. putrefacines* 8073, *P. maltophilia* 13673; *P. fluorescens* 13525; *P. cepacia* 17759; *P. putida* 12633 were also obtained for comparative purposes. The above strains were grown on trypticase-soy-agar (TSA) in single-neck round-bottom flasks enclosed with cotton plugs and incubated at 37° C. for 24 hours. These round-bottom flasks (250 ml) were fitted with a nitrogen inlet tube and an outlet tube which was attached to a 6 in.×⅜in. stainless steel tube containing 70 mg of Tenax GC (Applied Science), a porous polymer with good absorption properties and thermal stability. The headspace of the culture was swept with nitrogen at a flow rate of 80 ml/min. for 2 hours at 37° C.

The collected volatiles were then backflushed with heating (220° C. for 10 min.) onto the first 15 cm of the gas chromatographic (GC) column which was cooled with dry ice. The volatiles were then separated and identified by combined gas chromatography-mass spectrometry (GC/MS). The GC column was a 10 ft.×2 mm pyrex 20 M Carbowax on 80/100 Gas Chrom Q programmed at 70° C. (4 min), 70-220° C. (4° C./min). The GC/MS system was a Perkin-Elmer 990 GC interfaced with a Watson-Biemann separator to a Hitachi/PerkinElmer RMU-6L mass spectrometer. The mass spectrometer conditions included: ionizing voltage of 70 eV; source temperature at 200° C. and temperature of interface at 260° C. The mass spectra were recorded on a B and F model 3006 oscillographic recorder and interpreted manually. Individual components were identified by comparison of their fatty acid ethyl ester (FAEE) retention indices on a Carbowax column with those previously reported by van den Dool, et al, "A generalization of the retention index system including linear programmed gas-liquid chromatography", Journal of Chromatography, Vol. 11, pgs. 463–471 (1963); and by Withycombe, et al, "Isolation and identification of volatile components from wild rice grain", Journal of Agricultural Food Chemistry, Vol. 6, pgs. 816–821 (1978); and further by comparison of retention times and mass spectral data with authentic samples.

The procedure for the direct headspace analysis of cultures for volatile sulfur metabolites have employed a GC equipped with a flame photometric detector (FPD). It is essentially the same as the system described by Tonzetich in his paper entitled "Direct gas chromatographic analysis of sulfur compounds in mouth air in man", which appeared in the Archieves of Oral Biology, Vol. 16, pgs. 587–597 (1971). This system has been modified to the extent that a Perkin-Elmer 3920B GC with a 6-port injector valve (from Valco Instruments Co., Houston, Texas) and all Teflon ® (polytetrafluoroethylene) were used.

In accordance with the preferred embodiment of the present invention, the nature and extent of *Pseudomonas aeruginosa* infections may be determined by collecting, from a patient, a sample of material associated with the site of the suspected infection, collecting volatile compounds released from said sample to provide a sample headspace, and analyzing volatile compounds contained in said headspace to determine the concentration of one or more selected ketones contained in said headspace, whereby, the relative concentration of said ketone is diagnostic of the nature and extent of said *Pseudomonas aeruginosa* infection. Selected ketones in accordance with this embodiment include 2-nonanone and/or 2-undercanone.

Preferred samples for collection include samples of skin, sputum, breath, saliva, urine or other tissue which is suspected of containing *P. aeruginosa*, or of reflecting the metabolites of an existing *P. aeruginosa* infection. When the sample to be collected is a tissue, sputum, saliva, pus, urine or other solid or liquid material, it is advantageous to transfer that material to a collection vessel defining a headspace of known volume, which vessel may be used to collect or aid in the collection of, volatile compounds released from said sample, and, as desired, also be used for purposes of sample incubation and/or enhancement.

The preferred methods of collecting samples of breath, salvia or sputum are relatively simple, particularly when concentration of trace volatile metabolites from the biological sample on a solid absorbent followed by thermal desorption onto the front of the GC column is used. See Zlatkis, supra., (1973). For salivary headspace analyses, for example, each subject may be asked to donate a maximum of 10 ml of gum base stimulated saliva within a ten minute period. In some cases, saliva may be collected after mouth air samples have been obtained. 5 ml of this saliva may then be placed into a pre-cleaned 25 ml round bottom flask which may, as desired, contain an internal standard, nutrient additions, agar, etc. The flask may be then be sealed and incubated for pre-selected periods of time, as for example between one and five hours, under a pre-selected nitrogen flow of, for example, 100 ml/min with volatiles collected on Tenax.

In this manner, it is possible to incubate saliva and collect volatiles above it. Since incubation may continue, a series of collections may be made at various time intervals.

Presently, it is anticipated to utilize diethylphthalate as an internal standard. Use of this internal standard will permit calculations to be made concerning the amount of volatiles recovered from the headspace permitting ready conversion of data obtained by microgram quantities.

Sputum may be collected from patients by requesting those patients to cough up fluid. This is not difficult for patients with respiratory infections or CF patients with lung infections. Once obtained, sputum samples may be processed as described above in connection with saliva. For sampling lung air, subjects may be asked to forcibly exhale either into a Teflon ® bag through a Teflon ® valve or into a small tube containing Tenax absorbent. See MacKay (1978), supra. The contents of the Teflon ® bag may be transferred directly to the GC loop for analysis. The Tenax absorbed sample will be processed as described above for the transfer of volatiles. Alternatively, these methods may be combined by transferring the sample collected in the bag to the Tenax absorbent. The above mentioned MacKay article describes a method for concentrating lung air using Tenax. Such techniques may be utilized in accordance with the present invention for concentrating lung air.

It is also within the scope of the present invention to collect samples in a gaseous form, as for example by collecting breath or air which is otherwise located in the vicinity of a suspected *Pseudomonas aeruginosa* infection. For example, gases located in the immediate vicinity of the skin of burn patients or breath from lung patients, may be collected for this purpose without actually collecting any skin or other tissue samples which are primary sites of the *P. aeruginosa* infection. While such techniques somewhat increase the difficulty of sample collection, and may not lend themselves to sample enhancement techniques such as those described hereinafter, such techniques do have the advantage of minimally impacting the area of suspected infection.

In accordance with one alternate embodiment of the present invention, samples which are collected from a patient are incubated for a selected period of time. In most instances, incubation at 37° C. for between 1-24 hours prior to performing headspace analysis will act to predictably increase the concentration of volatile components to be detected. More particularly 3-8 hours, and preferably about 5 hours, have been found to be sufficient incubation periods for this purpose. In further embodiments of the present invention, collected samples are incubated together with materials which will predictably increase concentrations of the headspace compounds to be detected. For 2-nonanone, the subject samples may be incubated with additions of decanoic acid, and for 2-undercanone such additions may include additions of dodecanoic acid. Such concentrations may also be predictably increased through addition of nutrients such as 3-hydroxy-decanoic acid and 3-hydroxy-dodecanoic acid. As described more fully hereinafter, concentrations of methyl mercaptan may be increased by adding methionine to the incubation mixture. Alternatively, the sample may be transferred to a culture medium which is known to facilitate the growth of *Pseudomonas aeruginosa* and to produce the particular compound to be detected. For example, such culture medium may comprise trypticase soy agar or any other culture medium which predictably promotes the growth of *Pseudomonas aeruginosa* and its production of the particular volatile compounds to be detected.

Quite surprisingly, applicants have found that *P. aeruginosa* will release a series of odd-carbon methyl ketones, particularly 2-nonanone and 2-undecanone. In Table 1, which is set forth below, the concentration of methyl ketones determined in volatile profiles of *P. aeruginosa* are set forth for the various strains of *P. aeruginosa* referred to above.

TABLE 1

| Concentration of Methyl Ketones in Volatile Profile of *P. aeruginosa* | | |
|---|---|---|
| *P. aeruginosa* strain | Nonanone* | Undecanone* |
| ATCC 17429 | 0.13 | 0.19 |
| ATCC 17423 | 0.14 | 0.05 |
| ATCC 27313 | 0.30 | 0.15 |
| ATCC 27312** | 0.12 | 0.14 |
| ATCC 27316** | 0.25 | 0.23 |
| ATCC 7701 | 0.20 | 0.15 |
| CDC 9171 | 0.11 | 0.19 |
| CDC 9104 | 0.11 | 0.13 |

*Concentration in μg based on comparison of intensity of mass spectra peak m/z 58 with known amounts of 2-nonanone (38 mm/0.1 μg) and 2-undecanone (36 mm/0.1 μg).
**average of two runs The characteristic m/z 58 ion in the mass spectra of methyl ketones is formed by the well known 'McLafferty rearrangement'. See Budzikiewicz, et al, "Mass spectrometry of organic compounds", pg. 155, Holden-Day, Inc., San Francisco (1967). Consequently, increased sensitivity and selectivity where the presence of methyl ketones in pure and mixed cultures can be obtained by single-ion monitoring of GC effluent at this mass in combination with FAEE retention indices. In FIG. 1, the volatile of *P. aeruginosa* is illustrated with its peaks being identified for various methyl ketones which are identified by the formula:

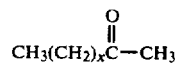

Figure 2:
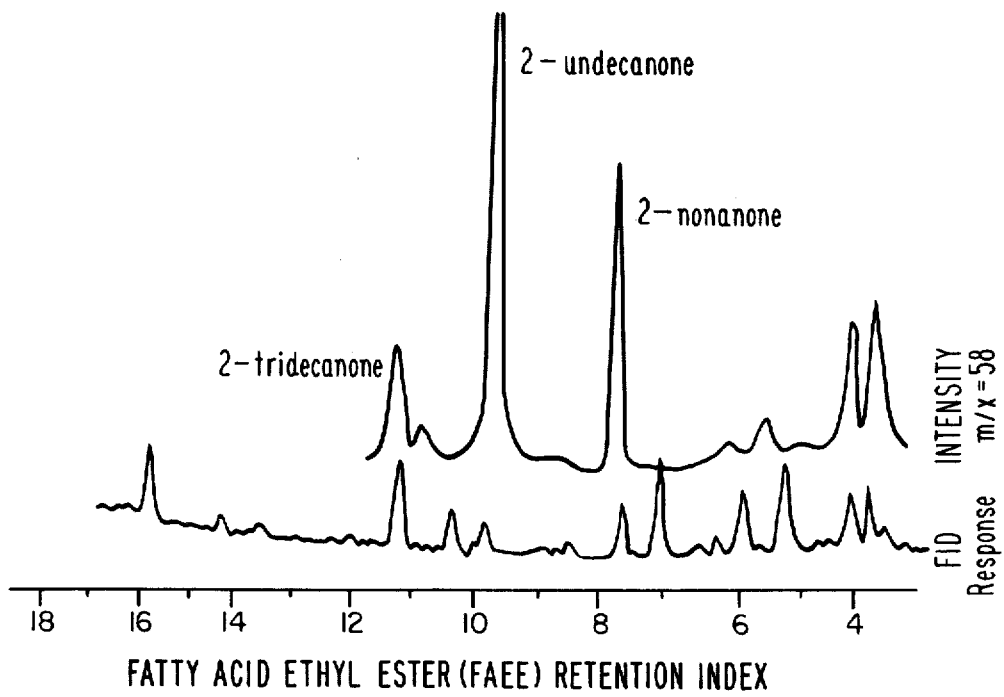
FIG. 2 is a volatile profile of *Pseudomonas aeruginosa* with single-ion-montoring, also showing the fatty acid ethyl ester (FAEE) retention index, and peaks for 2-tridecanone, 2-undercanone and 2-nonanone.

In FIG. 1, peaks are identified per 4, 5, 7, 9, 11 and 13 carbon atom methyl ketones. (Ketones wherein the value of x in the above identified formula is 1, 2, 4, 6, 8 and 10, respectively.) Single-ion monitoring using the above mentioned technique produces the m/z profile illustrated in FIG. 2, which provides an increased sensitivity and selectivity for the presence of methyl ketones in pure and mixed cultures. By comparison to the concentrations obtained from *Pseudomonas aeruginosa*, *Pseudomonas maltophilia* and *Pseudomonas putida* showed significantly reduced amounts of 2-nonanone, and trace levels of 2-undecanone, indicating that the present method is capable of distinguishing from these closely related species.

Figure 3:
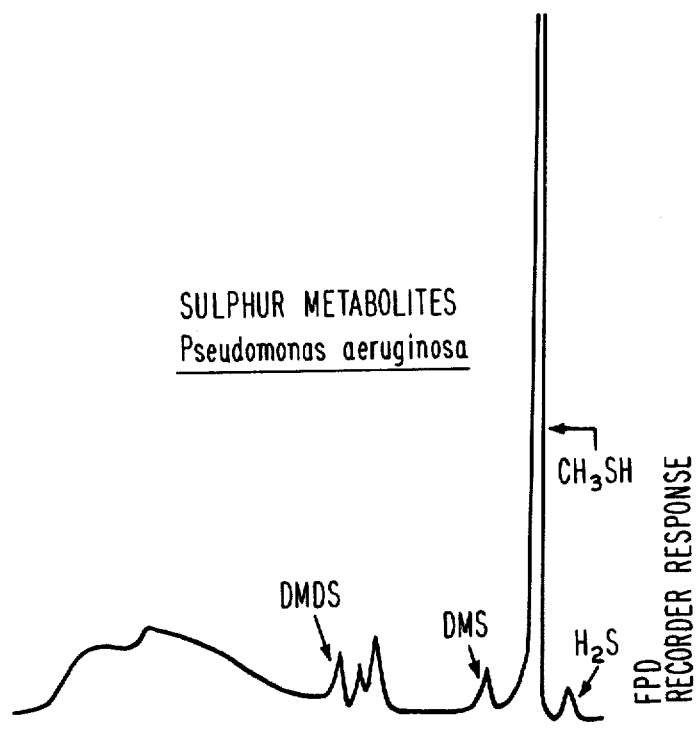
FIG. 3 is a profile of sulfur metabolites of *Pseudomonas aeruginosa* by direct headspace analysis, with various peaks thereof having been identified as being dimethyldisulfide (DMDS), dimethyl sulfide (DMS), $H_2S$, and $CH_3SH$.

In accordance with alternate embodiments of the present invention, the nature and extent of *P. aeruginosa* infections may be determined by analyzing for headspace concentrations of methyl mercaptan. As illustrated particularly in FIGS. 1 and 3, 2 sulfur metabolites, dimethyldisulfide (DMDS) and dimethyltrisulfide (DMTS) were present for all strains of *P. aeruginosa*, and in variable amounts in other species. Although the peak for DMTS was overlapping with 2-nonanone, its presence could be determined from its unique mass spectrum (m/z 126, 94, 79, 64, 61). In addition, the presence of methyl mercaptan could be shown by direct headspace sampling (10 ml) of the cultures (FIG. 3). No DMTS and only trace amounts of DMDS could be found without headspace concentration. A previous report indicates the presence of DMDS, but not methyl mercaptan, in cultures of *P. aeruginosa*. See Hayward, supra, Journal of Clinical Microbiology, Vol. 6, pgs. 195-201. 2-aminoacetophenone (2-AA) was also routinely detected using the headspace sampling technique reported here for all strains of *P. aeruginosa*. 2-aminoacetophenone has previously been reported to be present in ether extracts of *P. aeruginosa* cultures. Cox, supra, Journal of Clinical Microbiology, Vol. 9, pgs. 479-484.

Butanol, toluene, 2-butanone, 1-undecene, and isopentanol are the other components routinely observed in the Pseudomonas cultures. Long incubations (7 days) and collection times (17 hours) showed basically the same profile for *P. aeruginosa* with increased peak intensity for 2-AA and the presence of 4-methyl-quinazoline, a reaction product of 2-AA. Table 2, which is set forth below, summarizes the relative peak intensities for the strains of *P. aeruginosa*, and for the other Pseudomonads studied. In all samples reported here mass spectral data were used to confirm the identity of the GC peaks. Uninocculated culture media showed several volatile components including methyl-, dimethyl- and trimethylpyrazines, phenol, benzaldehyde, acetophenone, 2-ethyl-1-hexanol, and alkyl benzenes. Dimethyl-pyrazine was present in all cultures at an average GC peak intensity of 33 cm (m/z 108 68 mm).

TABLE 2

| | Relative Intensities of Volatile Components of Pseudomonads[a] | | | | | |
|---|---|---|---|---|---|---|
| | DMDS | Butanol + Undecene | Isopentanol | DMTS + 2-Nonanone | 2-Undecanone | 2-AA |
| *P. aeruginosa* | | | | | | |
| ATCC 19660 | 6 | 50 | 16 | 17 | 20 | 14 |
| ATCC 7700 | tr | 30 | 80 | 42 | 30 | 6 |

TABLE 2-continued

Relative Intensities of Volatile Components of Pseudomonads[a]

|  | DMDS | Butanol + Undecene | Isopentanol | DMTS + 2-Nonanone | 2-Undecanone | 2-AA |
|---|---|---|---|---|---|---|
| ATCC 27312[b] | 10 | 40 | 20 | 45 | 20 | 24 |
| ATCC 27316[b] | 21 | 45 | 22 | 29 | 16 | 17 |
| ATCC 27313 | 6 | 15 | 50 | 40 | 9 | ? |
| ATCC 7701 | 6 | 12 | 31 | 25 | 13 | 3 |
| ATCC 17429 | 22 | 55 | 100 | 85 | 17 | 50 |
| CDC 9171 | 26 | 40 | 50 | 40 | 23 | 40 |
| CDC 9104 | 3 | 5 | 7 | 5 | 3 | 14 |
| P. cepacia |  |  |  |  |  |  |
| ATCC 17759 | 12 | — | — | 4[d] | — | — |
| P. putrefaciens |  |  |  |  |  |  |
| ATCC 8073 | 60 | 60[c] | 960 | 4[d] | — | — |
| P. maltophilia[b] |  |  |  |  |  |  |
| ATCC 13637 | tr | 50[c] | 1200 | 4[d] | 3 | — |
| P. flourescens |  |  |  |  |  |  |
| ATCC 13525 | — | 50[c] | 640 | 8[d] | — | — |
| P. putida |  |  |  |  |  |  |
| ATCC 12633 | 120 | 10[c] | 20 | 27[d] | 2 | — |

[a]Values are relative GC peak intensities (cm) on $1 \times 10^{-10}$ with ½ material going to the mass spectrometer. Volatiles were concentrated on Tenax (2 hrs; 80 ml/min) and transferred with heating to the gas chromtograph prior to analysis.
[b]Average of two runs.
[c]Only butanol
[d]Mainly DMTS It is theorized that the series of odd-carbon numbered methyl ketones reported here for P. aeruginosa may be formed from the beta oxidation and decarboxylation of even-carbon numbered fatty acids. Similar ketone series have been observed in other biological systems. See Dwivedi, et al "Carbonyl production from lipolyzed milk fat by the continuous mycelial culture of Penicillium roqueforti." J. Food Science, 39:83–37 (1974). The odor of the pedal gland of the bontebok was reported to be due to 2-heptanone, 2-nonanone, 2-undecanone and principally 5-undecen-2-one. See Burger, et al "Ketones from the pedal gland of the bontebok", Z. Naturforsch C: Bioscience 316:(1–2):21–8. It is not known whether the odor is produced by the pedal gland of the bontebok are products of bacterial composition, as has been reported to be the case in pheromonal production in other mammals. See Albone, et al, "Bacterial as a source of chemical signals in mammals", reprinted at pages 35–43 in D. MullerSchwarze and M. M. Mozell, editors, Chemical signals in vertebrates, Plenum Press, New York (1977). It has been suggested that the ovipositional attractant for mosquitos is related to P. aeruginosa, and that the active compounds are produced from the action of this organism on fatty acids substrates, particularly decanoic acid. See Ikeshoji, "Bacterial production of the ovipositional attractants for mosquitos on fatty acid substrates", Appl. Ent. Zool. 10:239–242. Penicillium roqueforti is known to readily transform fatty acids in lipolyzed milk fat to 2-pentanone, 2-heptanone, 2-nonanone and 2-undecanone which contribute to the blue-cheese odor. See Dwivedi, supra. In this context, a mechanism based on the deacylation of beta-oxo-acyl-thiolester has been suggested for ketone formation. In other reports, the presence of differing amounts of 3-hydroxy-decanoic and 3-hydroxy-dodecanoic acids have been suggested as one means of discriminating between Pseudomonas species. See Moss, supra.

It is theorized that the effectiveness of additions of organic acids, such as decanoic and dodecanoic acids to an incubating sample mixture to increase headspace concentrations of 2-nonanone and 2-undecanone is explained by the metabolism of such substrates by P. aeruginosa present in the test sample. Data reported in the above mentioned literature, although not relating to the production of such ketones, is not inconsistent with the metabolic pathway theorized by applicants. It is noted, for example, that P. fluorescens, P. aeruginosa and P. putida show similar levels of the above mentioned 3-hydroxy acids. As seen from Table 2, both P. aeruginosa and P. putida produced both ketones, while P. fluorescens produces 2-nonanone. Similarly, various secondary metabolites of P. aeruginosa comprise beta-keto-decanoic-acid or beta-hydroxy-decanoic acid, as well as decanoic acid. Certain of these materials have been identified as constituents of the lipopolysaccharide component of the outer membrane of certain gram-negative bacteria including pseudomonads. See Leisinger, et al, supra. It is possible that the 2-nononane which has been detected through our studies is a metabolite of these acids, which are found in cultures of the pseudomonads.

In any event, it has been found that the addition of these potential precursors to incubated sample mixtures will generally substantially reduce the incubation time necessary to obtain concentrations permitting a definitive diagnosis of the nature and extent of Pseudomonas aeruginosa infections in the subject patients. Since, at the present time, a five hour incubation period is preferred, the methods of the present invention reduce the time required to diagnosis such infections, when compared to traditional culturing techniques.

The present invention thus provides a simple, relatively economical, rapid species-specific test which is diagnostic of the nature and extent of Pseudomonas aeruginosa infections. Using the methods of the present invention, it should be possible to rapidly and optimally treat such infections, and thus, to substantially improve the recovery and survival rates of patients suffering from such infections.

What is claimed is:

1. A method of diagnosing the nature and extent of a suspected Pseudomonas aerguinosa infection, comprising:
(a) collecting from a patient suspected of having such infection, a sample of material associated with the site of such suspected infection;
(b) collecting volatile compounds released from said sample to provide a sample headspace;

(c) analyzing said sample headspace; and
(d) determining the concentration of least one methyl-ketone contained in said headspace, said methyl ketone having the formula:

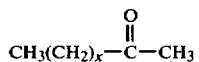

where X is 1, 2, 4, 6, 8 or 10 to thereby diagnose the nature and extent of such infection.

2. The method of claim 1 wherein said at least one methyl-ketone is a methyl-ketone containing between four and thirteen carbon atoms.

3. The method of claim 2 wherein said methyl-ketone is a methyl-ketone having an odd number of carbon atoms numbering between five and thirteen.

4. The method of claim 3 wherein said methyl-ketone is a methyl-ketone having between nine and thirteen carbon atoms.

5. The invention of claim 1 wherein said methyl-ketone is 2-nonanone.

6. The method of claim 1 wherein said methyl-ketone is 2-undecanone.

7. The method of claim 1 wherein said sample is a sample of animal tissue biopsied from the site of such suspected infection.

8. The method of claim 1 wherein said site of such suspected infection is the skin, and wherein such sample collected is a sample of skin.

9. The method of claim 1 wherein said site of such suspected infection is within the respiratory system, and wherein such sample is sputum.

10. The method of claim 1 wherein such site is within the respiratory system and wherein said sample is saliva.

11. The method of claim 1 comprising the additional step of incubating said sample to provide a sample headspace.

12. The method of claim 11 wherein said incubating continues for between one and twenty-four hours.

13. The method of claim 12 wherein said incubating is performed for between three and eight hours.

14. The method of claim 13 wherein said incubating is performed for about five hours.

15. The method of claim 11 further comprising the step of enhancing the concentration of said at least one methyl-ketone contained in said headspace by incubating said sample with at least one nutrient, which, under the conditions of incubation, predictably increases the concentration of at least one such methyl-ketone in said headspace.

16. The method of claim 15 wherein said at least one methyl ketone is 2-nononane, and wherein said additional nutrient comprises decanoic acid.

17. The method of claim 15 wherein said nutrient is 3-hydroxy-decanoic acid.

18. The method of claim 15 wherein said at least one methyl-ketone is 2-undecanone, and wherein said nutrient comprises dodecanoic acid.

19. The method of claim 15 wherein said nutrient comprises 3-hydroxy-dodecanoic acid.

20. The method of claim 15 wherein said nutrient is a *Pseudomonas aeruginosa* growth medium.

21. The method of claim 20 wherein said growth medium is trypticase soy agar.

22. A method of diagnosing the nature and extent of a suspected *Pseudomonas aeruginosa* respiratory infection, comprising:
(a) collecting a breath sample from a patient suspected of having said infection;
(b) analyzing said breath sample; and
(c) determining the concentration of at least one methyl-ketone contained in said breath sample, said methyl-ketone having the formula:

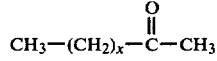

where X is 1, 2, 4, 6, 8 or 10 to thereby diagnose the nature and extent of such infection.

23. The method of claim 22 wherein said at least one methyl-ketone is a methyl-ketone having an odd number of carbon atoms between nine and thirteen.

24. The method of claim 23 wherein said methyl-ketone is 2-nonanone.

25. The method of claim 22 wherein said methyl-ketone is 2-undecanone.

26. A method of diagnosing the nature and extent of a suspected *Pseudomonas aeruginosa* infection comprising the steps of:
(a) collecting from a patient suspected of having said infection a sample of a material associated with the site of such suspected infection;
(b) incubating said sample with at least one additional substance which is selected to increase the quantity of methyl mercaptan released by said sample during incubation;
(c) collecting volatile compounds related from said sample during said incubation to provde a sample headspace;
(d) analyzing said sample headspace; and
(e) determining the concentration of said methyl mercaptan contained in said headspace to thereby diagnose the nature and extent of such infection.

27. The method of claim 26 wherein said additional substance is methionine.

28. The method of claim 26 wherein said additional substance is a growth medium.

29. The method of claim 28 wherein said growth medium is trypticase soy agar.

30. A method of diagnosing the nature and extent of a suspected *Pseudomonas aeruginosa* infection comprising the steps of:
(a) collecting from a patient suspected of having said infection a sample of material associated with the site of such suspected infection;
(b) collecting volatile compounds released from said sample to provide a sample headspace;
(c) analyzing said sample headspace; and
(d) determining the concentration of methyl-mercaptan contained in said headspace to thereby diagnose the nature and extent of such infection.

* * * * *